United States Patent [19]
Haldemann et al.

[11] Patent Number: 5,473,248
[45] Date of Patent: Dec. 5, 1995

[54] METHOD AND APPARATUS FOR NON-DESTRUCTIVELY DETECTING FLAWS IN A CARBON ANDODE

[75] Inventors: Paul R. Haldemann, College Park; Eman P. Fawzi, Gaithersburg, both of Md.

[73] Assignee: The University of Maryland at College Park, College Park, Md.

[21] Appl. No.: 416,540

[22] Filed: Apr. 3, 1995

Related U.S. Application Data

[63] Continuation of Ser. No. 101,033, Aug. 3, 1993, abandoned.
[51] Int. Cl.$^6$ ............................ G01N 27/72; G01R 33/12
[52] U.S. Cl. ........................ 324/238; 324/227; 324/237; 324/718; 204/401
[58] Field of Search ........................... 324/227, 237, 324/238, 232, 240, 718; 204/401, 294, 280

[56] References Cited

U.S. PATENT DOCUMENTS

| | | | |
|---|---|---|---|
| 4,667,149 | 5/1987 | Cohen | 324/718 |
| 4,922,201 | 5/1990 | Vernon | 324/232 |
| 4,924,182 | 5/1990 | Vernon | 324/232 |
| 5,028,100 | 7/1991 | Valleau | 324/232 |
| 5,138,269 | 8/1992 | Deutsch | 324/718 |

*Primary Examiner*—Kenneth A. Wieder
*Assistant Examiner*—Jose M. Solis

[57] ABSTRACT

A system and method of automatic, in-line electrical quality control of a carbon anode including detecting internal flaws in the carbon anode by measuring an eddy-current loss of the carbon anode and determining intrinsic resistivity of the carbon anode by measuring resistivity of the carbon anode and determining the electrical quality of the carbon anode according to the measured eddy-current loss and the measured resistivity.

40 Claims, 14 Drawing Sheets

12
METHOD AND APPARATUS FOR NON-DESTRUCTIVELY DETECTING FLAWS IN A CARBON ANDODE

This application is a continuation, of application Ser. No. 08/101,033 filed on Aug. 3, 1993, now abandoned.

The present invention relates to a method and system for non-destructively detecting flaws in a carbon anode, by detecting internal flaws of the anode based on an eddy current loss measurement and measuring the intrinsic resistivity of the anode using a four point resistivity measurement. Together, the two measurements give an indication of the quality of the anode.

BACKGROUND OF THE INVENTION

In order to make primary aluminum by a conventional technique known as an electrolytic process, large carbon blocks are utilized as anodes. In order for these anodes to work efficiently and reliably, it is important that the carbon blocks have low electric resistivity and are free from internal flaws and cracks. Therefore, it is important for a primary aluminum producer to test the carbon anodes for internal flaws and low resistivity before they are used in the actual process for producing primary aluminum.

In conventional techniques, the primary aluminum producer must extract a core sample from a baked anode in order to perform the electric resistivity and internal flaw detection test. The core sample must be removed and sent to a laboratory in order for the measurements discussed above to be made. Once the results come back from the laboratory, these results are obsolete because the anodes which were produced concurrently with the core sample which was tested, have already been installed in an aluminum production pot line, and are either working fine or have already failed.

As a result, there exists a need for the primary aluminum producer to automatically and non-destructively test anodes in an in-line test setup for internal flaws and low resistivity, so that low quality anodes may be discarded before they fail in the production line. Several techniques, which have been proposed, are discussed below.

A first proposed technique for detecting the internal flaws in a carbon anode utilizes a change in DC resistance of the carbon block. At every contact point, the current enters the carbon block and spreads out into the carbon volume. Since the cross-section near the contact point, through which the current travels, is much smaller than further away, the total resistance of the current path is dominated by the resistance near the contact point. If the material has no random irregularities, this would not present a serious problem. However, in reality, the carbon blocks utilized as anodes in the electrolytic process contain thousands of such local irregularities which completely dominate the change in resistance. As a result, the change in DC resistance is not an accurate indication of internal flaws in the carbon anode. Still further, contact wear and the bridging of current and potential contact points by carbon dust are additional problems which may make internal flaw detection unfeasible by this approach.

A second proposed technique involves the use of ultrasonic sound to detect flaws in the carbon anode. However, the problems discussed above with respect to the DC resistance measurements are even more severe. In this technique, the signal reflected from flaws is used to detect cracks in the interior of the anode. Since the carbon block has thousands of irregularities which all produce back scattering, it is nearly impossible to distinguish random back scatter and backscatter from actual flaws. This distinction is even made more difficult because the random scattering attenuates the signal rapidly as it travels through the carbon block, so that random back scattering from a location close to the transducer can be much stronger than the back scattering from a serious flaw in the middle of the carbon block. In addition, this strong attenuation requires a large amount of energy to be coupled into the carbon block, which in turn produces even more random back scattering. As a result, the ultrasonic method is also unfeasible for carbon anodes.

As a result of the failures discussed above with respect to the DC resistance measurement and ultrasonic techniques, it is probable that any electrical measurement would have to be made such that the physical contact between the measuring device and the carbon block does not influence the measurement. Further, if sound waves are to be utilized, the energy coupling problem must be eliminated and scattering and attenuation must be drastically reduced.

One final technique which provides potentially promising results is an audio sound flaw detection method. For example, if two different carbon blocks are hit with a hammer, the sound generated by each is significantly different. Such an audio sound flaw detection system would eliminate the energy coupling problem present in the ultrasonic method and the much longer wavelength would reduce attenuation and back scatter. Further, preliminary measurements confirm that each carbon block appears to have its own distinct sound signature. This time domain signature can be converted into a frequency spectrum in order to reveal flaws in the carbon block. However, although it is a relatively simple task to convert the time domain signatures for each carbon block into frequency spectra, it is extremely difficult to determine which part of the spectrum represents flaws and which part illustrates the features of a good carbon anode. In order to successfully analyze the frequency spectra, this technique requires a homogeneous graphite block in order to calibrate the sound measurement instrumentation. Further, in order to ensure that the calibrations are free of environmental sound contamination, the calibration experiment would have to be conducted in an anechoic chamber, which is expensive.

The method and system of the present application solves the problems discussed above with respect to conventional carbon block analysis techniques, in that the method and system of the present application permit the primary aluminum producer to automatically and non-destructively test anodes in an in-line test setup, for internal flaws and high resistivity. Further, the method and system of the present application exhibit none of the problems discussed above with respect to the other conventional techniques. As a result, low quality anodes can be discarded at an early point in production.

The method and system of the present application utilizes two measurements in order to determine if a carbon block should be accepted or rejected for use in aluminum production. First, an eddy current loss measurement is made to detect the internal flaws of the anode, and second, a four-point resistivity measurement is made to measure the intrinsic resistivity of the anode. Together, these two measurements give an indication of the quality of the anodes.

SUMMARY OF THE INVENTION

One object of the present invention is to provide a method and system for determining the electrical efficiency with which a carbon anode performs in a pot line by determining its electrical resistivity after baking and by determining internal flaws, such as cracks, voids, and inclusions in the carbon anode block. Two electrical measurements are utilized to determine the electrical quality of the carbon anode. First, a four-point probe is used to determine the electrical resistivity, and second, the eddy current losses induced by a coil brought into proximity with the carbon anode are measured. The combined measurements by the user of the invention is to determine if an anode will function at high efficiency in an aluminum production pot line.

These objects of the present invention are fulfilled by providing a method of automatic in-line electrical quality control of a carbon anode, comprising the steps of:

a) detecting internal flaws in the carbon anode by measuring an eddy-current loss of the carbon anode;

b) determining intrinsic resistivity of the carbon anode by measuring resistivity of the anode; and c) determining the electrical quality of the carbon anode according to the measured eddy-current loss of said step (a) and the measured resistivity of said step (b).

The objects of the present invention are further fulfilled by providing a system for automatic in-line electrical quality control of carbon anodes, comprising:

internal flaw detecting means for detecting internal flaws in the carbon anode by measuring an eddy-current loss of the carbon anode;

intrinsic resistivity determining means for determining intrinsic resistivity of the carbon anode by measuring resistivity of the carbon anode; and electrical quality determining means for determining the electrical quality of the carbon anode according to the measured eddy-current loss and the measured resistivity of the carbon anode.

These and other objects of the present invention will become more readily apparent from the detailed description given hereinafter. However, it should be understood that a detailed description and specific examples, while indicating preferred embodiments of the invention, are given by way of illustration only since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only and thus are not limitative of the present invention and wherein.

DETAILED DESCRIPTION OF THE PREFERRED EMBODIMENTS

As discussed above, the method and system of the present application utilizes two measurements in order to determine if the carbon block should be accepted or rejected for use in an aluminum production process. First, an eddy-current loss measurement is made to detect the internal flaws of the anodes, and second, a four-point resistivity measurement is made in order to measure the intrinsic resistivity of the anodes. Together, these two measurements give an indication of the quality of the anodes.

Figure 1:
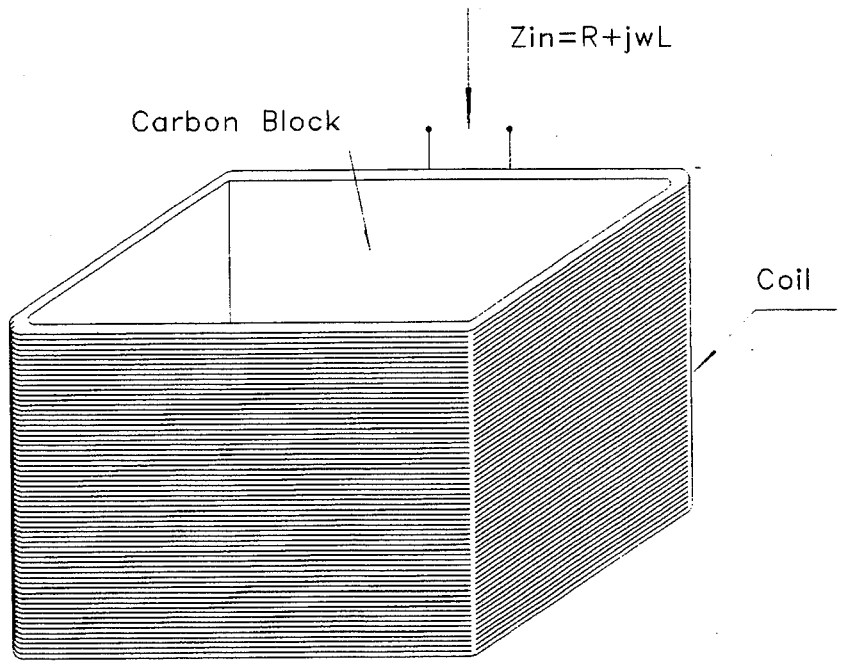
FIG. 1 illustrates a preferred embodiment of the present invention for measuring internal flaws in a test object.

Initially, the principles underlying the measurement of the eddy current in order to detect internal flaws in the carbon anode will be discussed. As illustrated in FIG. 1, a cylindrical coil closely matching the form of the test object is slid over the carbon anode block. Together the coil and the carbon block form a transformer, wherein the surrounding coil is the primary winding and the carbon block acts as a single turn secondary winding.

When the primary winding is excited by an alternating current, the magnitude and phase of the current induced in the carbon block is affected by the internal quality of the carbon block. By measuring the reflected impedance $Z_{in}$ of the input of the primary coil, it is possible to measure the internal quality of the block. High losses indicate good electrical quality and low losses indicate internal flaws and voids. It is also possible to use a flat coil for the loss measurements. In this case, the coils are brought into contact with the carbon block surface for the measurement. Further, multiple coils and coupled coils can be utilized in order to measure the reflected impedance.

Figure 2:
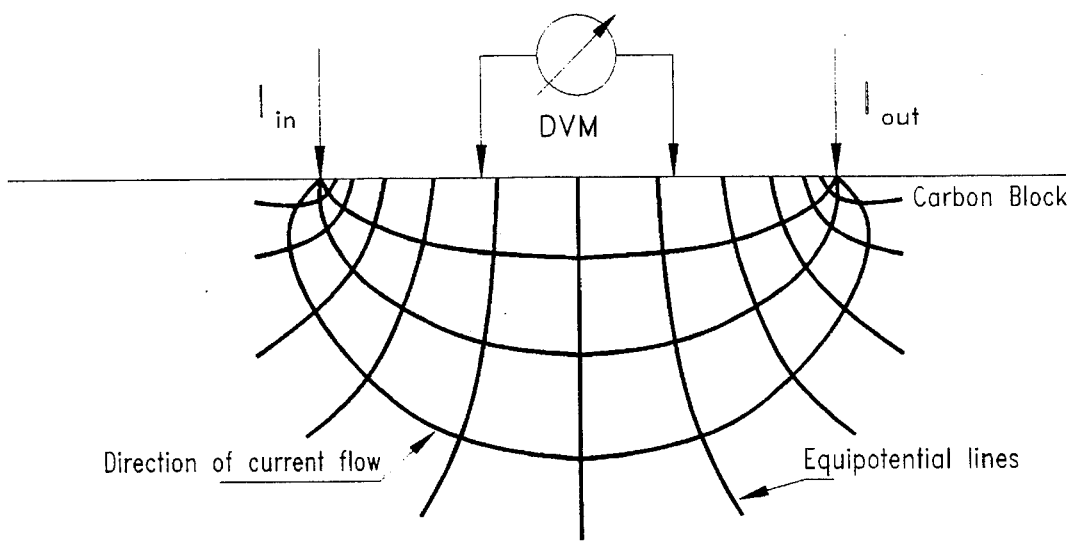
FIG. 2 illustrates a preferred embodiment of the present invention for measuring resistivity of the test object.

The measurement of the resistivity on a flat surface utilizing four resistivity probes is illustrated in FIG. 2. If two current carrying probes are placed on one surface of a rectangular block of conducting material, an electric potential distribution is generated inside the conducting body and on its surface. For appropriately chosen contact locations, the potential difference between two points on the surface is primarily represented by the resistivity of the conducting body. It is therefore, possible to calculate the resistivity from the potential difference measurement. In general, the four electrodes may be placed anywhere on the surface of the block. However, in a preferred embodiment, the four electrodes are placed in a straight line with the same spacing from electrode to electrode. Further, in the preferred embodiment, the outer electrodes are utilized as the current carrying electrodes and the two inner electrodes are utilized to measure the potential difference.

Since the surface of the carbon block is irregular, each contact must be spring-loaded to make good contact with the carbon surface. Stops are provided so that the contact force stays within a certain range. The contacts are accurately guided so that exact repeatable measurements can be made. Each contact is individually spring loaded to adjust to the surface irregularities of the carbon anode and guided by an adjustable linear twin ball bearing. Since linear ball bearings have a tendency to roll grooves into the hardest steel shafts, the contact and shaft assembly are made of single piece of tungsten carbide. The contact force is six pounds per contact which is very close to the value for which the measured resistivity changes minimally between values measured on a raw contact surface, a pre-drilled contact surface and settled in contacts on a raw surface. Further, the force needed on an arm which brings the device in contact with the carbon anode must be at least 24 lbs.

First, a detailed discussion of the eddy current measurement for detecting internal flaws in the carbon anode will be provided.

By subjecting a test sample, such as the carbon anode block, to an alternating magnetic field, losses may be measured which are a function of the composition of the test sample, the sample volume, the distribution of the aggregate, its baking history, and most importantly, cracks and flaws in the carbon anode block. The losses are especially high for cracks and flaws which run at right angles to the induced current flow. As a result, it is possible to design a coil which induces currents which flow at right angles to the plane of the most likely occurring cracks. Theoretically, changing the frequency of the magnetic field changes the depth of penetration of the induced current and provides a method for measuring how deep inside the carbon anode block the flaws are. The calculations of skin depth versus frequency illustrate that if it were possible to make measurements at 300 Hz, the entire carbon anode block could be penetrated. For this case, the coil would have to completely surround the carbon block.

The eddy current measurement is performed as follows. If a piece of conducting material is placed inside a coil, the conducting material acts as if it were a one-turn secondary winding of a transformer. The main difference is that the resistance, inductance, and capacitance of the conducting material are distributed elements. This makes the transformer strongly frequency dependent and difficult to simulate utilizing discrete circuit elements. In general, all laws which describe the relationship between the primary and secondary windings of a transformer apply to the conducting material surrounded by the coil. The most important characteristic which can be exploited is the fact that all electrical quantities of the one-turn secondary winding are transformed into the primary winding. Since, in the present application, the secondary winding is the carbon block under test, it is possible to measure how one carbon block differs electrically from another. Of all the transformed electrical qualities, such as the resistance, inductance, and capacitance, the resistance is directly related to the bulk resistance of the carbon block. The bulk resistance, is in turn related to resistivity and cracks in the carbon block. If a measurement can provide the value of the resistivity, then the amount of cracking present in the carbon block may be established.

Preliminary tests conducted with cylindrical carbon samples on a bridge circuit indicate that it is possible to detect differences between individual samples. Any computer addressable impedance measuring bridge may be utilized for this purpose. From skin depth calculations, measurements need to be made between 100 and 2,000 Hz. The impedance measuring range for which the measuring instrument must have high accuracy and resolution lies between 10 and 10,000 ohms. In addition, the instrument must be computer addressable and highly stable to temperature variation. In the preferred embodiment, the Hewlett-Packard 4284A High Precision RLC meter meets the above requirements. The coil of the system of the present application fits over the carbon blocks in such a way that the induced current flows largely in the same direction as the DC current flows when the carbon blocks are utilized as anodes in aluminum production. In a preferred embodiment, the dimensions of the coil are 32 inches (length) by 22 inches (width) by 22 inches (height). The coil has 336 turns of flat copper wire with an equivalent cross-section of an AWG #10 wire. Further, the coil has the following electrical characteristics:

$L$=71 Mh, $R_{DC}$=3.95 ohms, $Q_{max}$=71 at 2.5 KHz, $C$=5700 Pf, and $f_{peak}$=7900 Hz.

Figure 3:
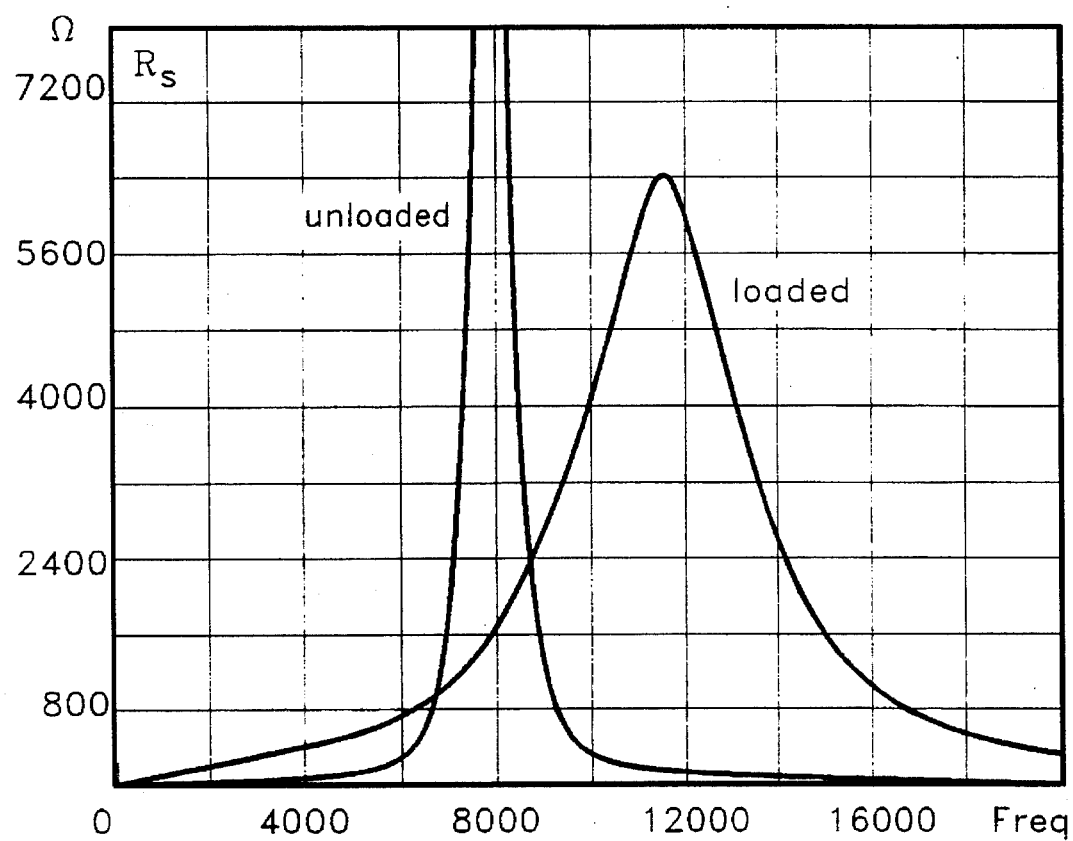
FIG. 3 is a graph of resistance vs. frequency of a loaded and unloaded large block surrounding coil.
Figure 4:
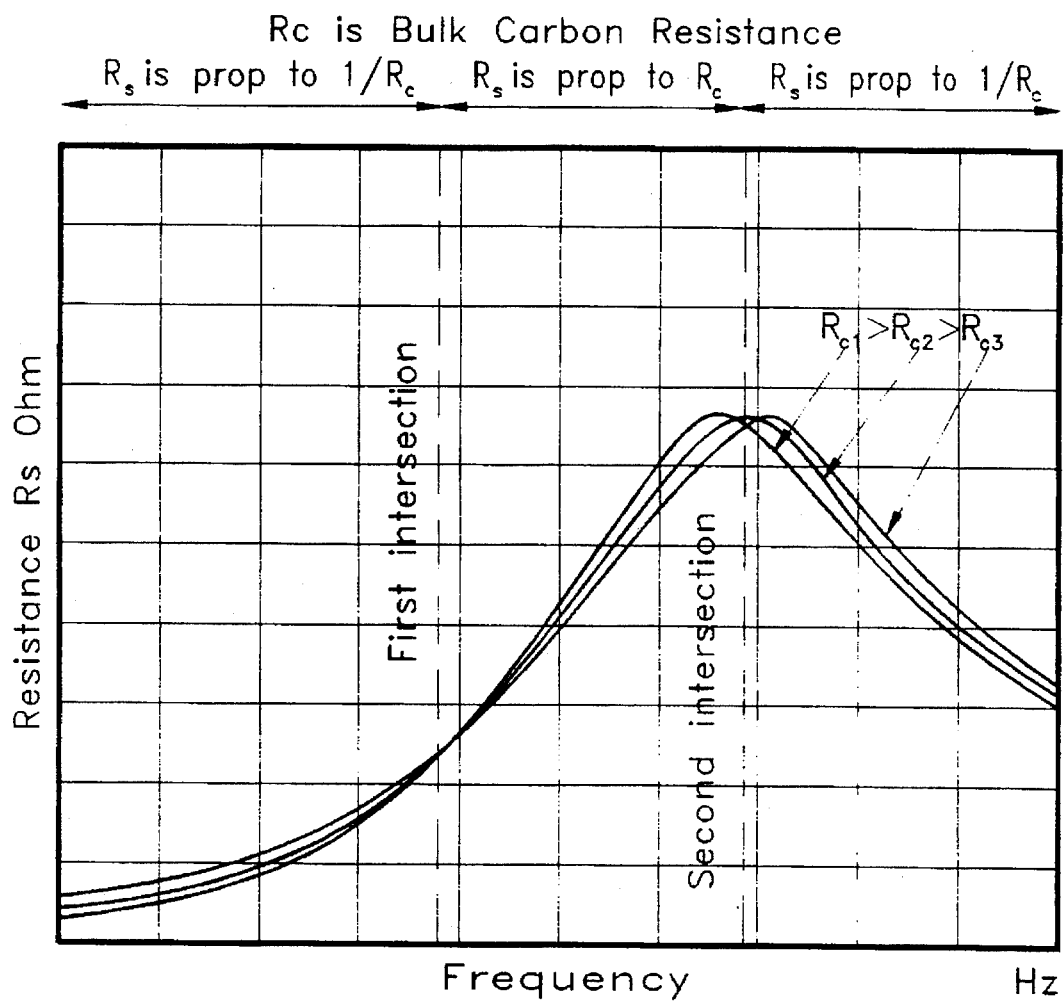
FIG. 4 is a graph of calculated input resistance vs. frequency for three different carbon block resistances.

Further, the coil's loaded and unloaded impedance, as a function of frequency, is illustrated in FIG. 3. FIG. 3 illustrates that adding a load reduces the resistance peak at resonance and shifts the resistance peak to a higher frequency. This lowering and shift of the peak is also true if a carbon block representing a higher load (lower bulk resistance) is inserted into the coil. FIG. 4 illustrates the predicted change of $R_S$ for three carbon blocks with progressively lower bulk resistance. These curves illustrate that any two resistance curves representing different loads always intersect at two frequencies. The two frequencies separate the curves into three regions.

Figure 5:
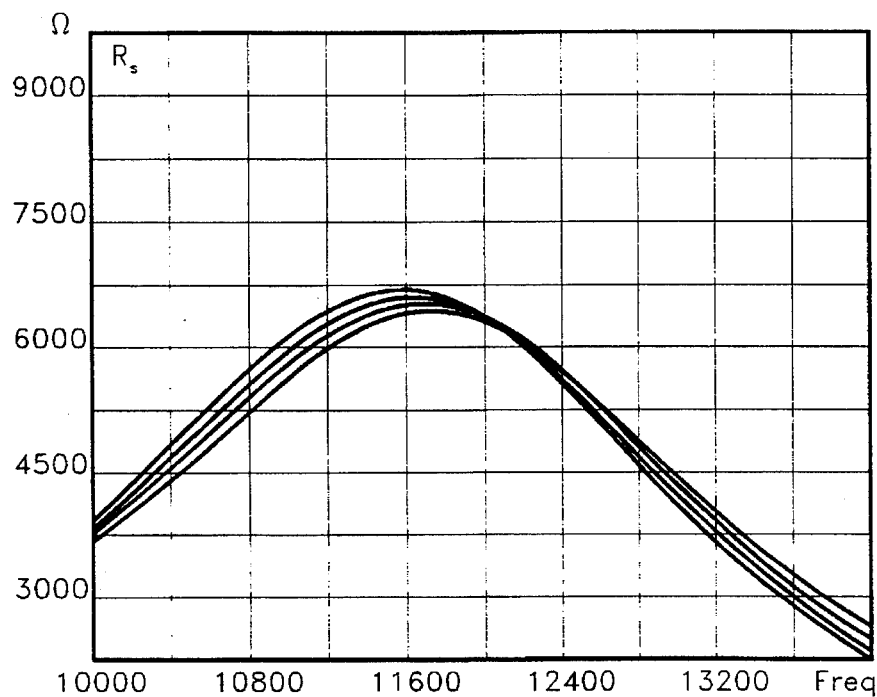
FIG. 5 is a graph of bulk resistance $R_S$ vs. frequency near the resistance peak for six carbon blocks measured with the large block surrounding coil.

In the region below the first intersection and in the region above the second intersection, a smaller bulk resistance indicates a higher resistance; and, the region between the intersections, which includes the peak resistance, the opposite is true, namely, a smaller bulk resistance indicates a lower resistance. FIG. 5 illustrates the results of actual measurements which confirm this phenomenon.

Utilizing the coil described above, in an in-line measuring system, poses some technical difficulties. Because it is desirable that the induced current flows mostly in the same direction as the DC operating current, the carbon block must be pushed broadside into the measuring coil with rod connectors facing the coil. This is accomplished in one of two ways: First, the upright block is pushed sideways into the measuring coil or second, the block is laid on its side and pushed up into an overhead coil. The technical difficulty in the first case arises from the fact that no metal rollers, which are required in the in-line measuring system, can be inside the coil or near the opening of the coil. Further, no other metal should be located within an 8 ft. spherical boundary of the coil. In the second case, the mechanism which turns the block sideways and pushes the block up into the coil also must be free of metal. One solution to this problem is to use wood or plastic rollers to move the block into the coil, however, most existing aluminum production facilities have metal rollers. Therefore, the use of non-metal rollers could result in a significant cost modification to an existing facility. Another solution, which overcomes these difficulties and is disclosed in another embodiment of the present application, utilizes a flat coil instead of the large block surrounding coil.

The flat coil utilized in another preferred embodiment of the present application is 3/16 inches thick and constructed with an outer diameter of 12 inches and an inner diameter of 6 inches. The coil has 300 turns of #18 copper wire. Its electrical characteristics are as follows:

$L_S$=26 Mh, $R_{DC}$=4.59 ohms, $Q_{max}$=70 at 3.2 KHz,

C=8800 Pf, and $F_{peak}$=10.7 KHZ.

Figure 6:
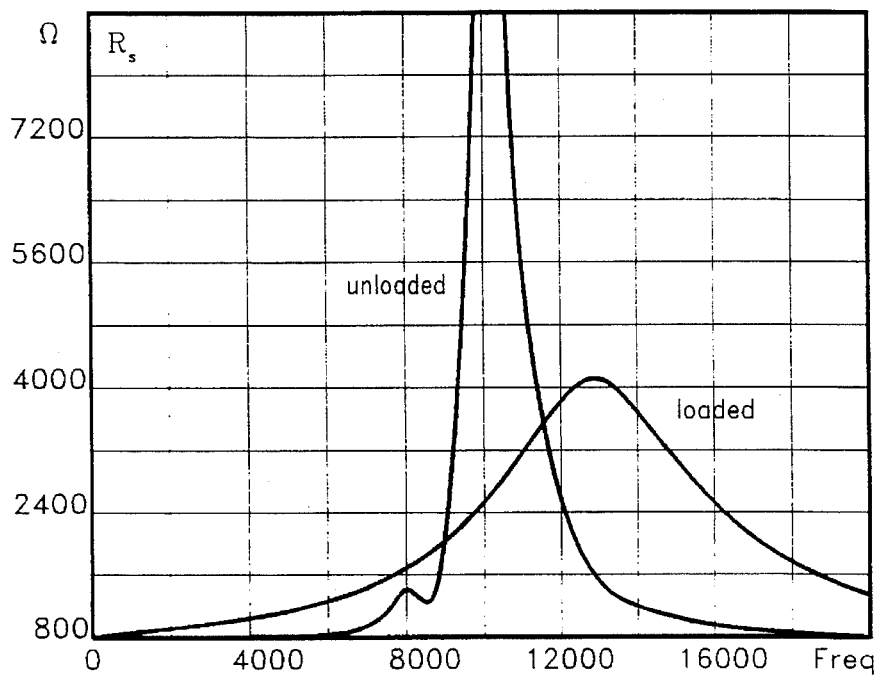
FIG. 6 is a graph of resistance vs. frequency of a loaded and unloaded flat coil.
Figure 7:
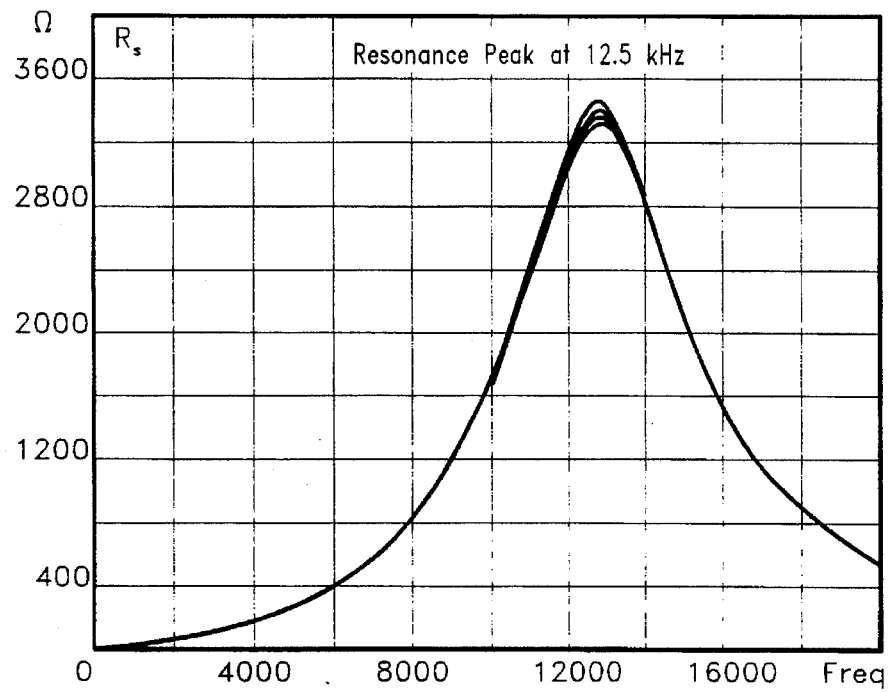
FIG. 7 is a graph of the bulk resistance $R_S$ vs. frequency near the resistance peak for six carbon blocks measured with the flat coil.
Figure 8:
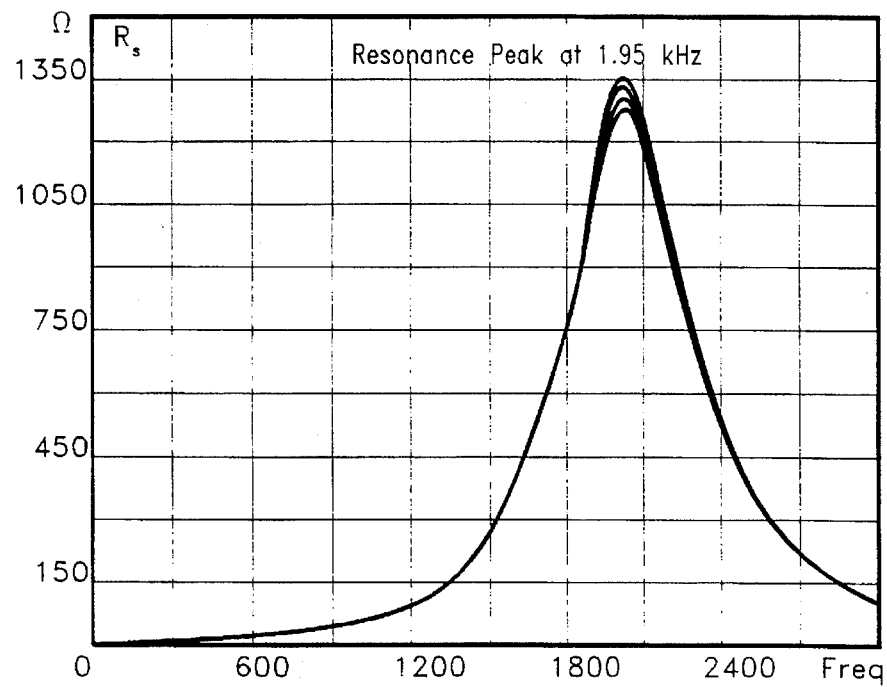
FIG. 8 is a graph of the bulk resistance $R_S$ vs. frequency near the resistance peak for six carbon blocks measured with the flat coil and a 0.25 µF capacitor in parallel.

When this coil is held against a carbon block and excited with an alternating current, a donut-shaped current flow is induced directly underneath the coil inside the carbon block. The lower the frequency, the deeper the current will penetrate. At 300 Hz, the current penetrates about halfway through the block. Therefore, it would be necessary to make a measurement on both sides of the carbon block in order to test the entire block volume. FIG. 6 illustrates the loaded and unloaded impedance responses as a function of frequency when the flat coil described above is held against the carbon block. Further, FIG. 7 illustrates the resistance response of several blocks, which illustrates that these results match the results obtained utilizing the large block surrounding coil. Further, the addition of a capacitor in parallel to the coil shifts the resonance peaks to a lower frequency. The results of adding a 0.25µF capacitor are illustrated in FIG. 8. Since the external capacitor dominates the circuit, there is little change in frequency at which R peaks for the various carbon blocks. This enables measurements to be made at the frequency of the resonance peaks.

Figure 9:
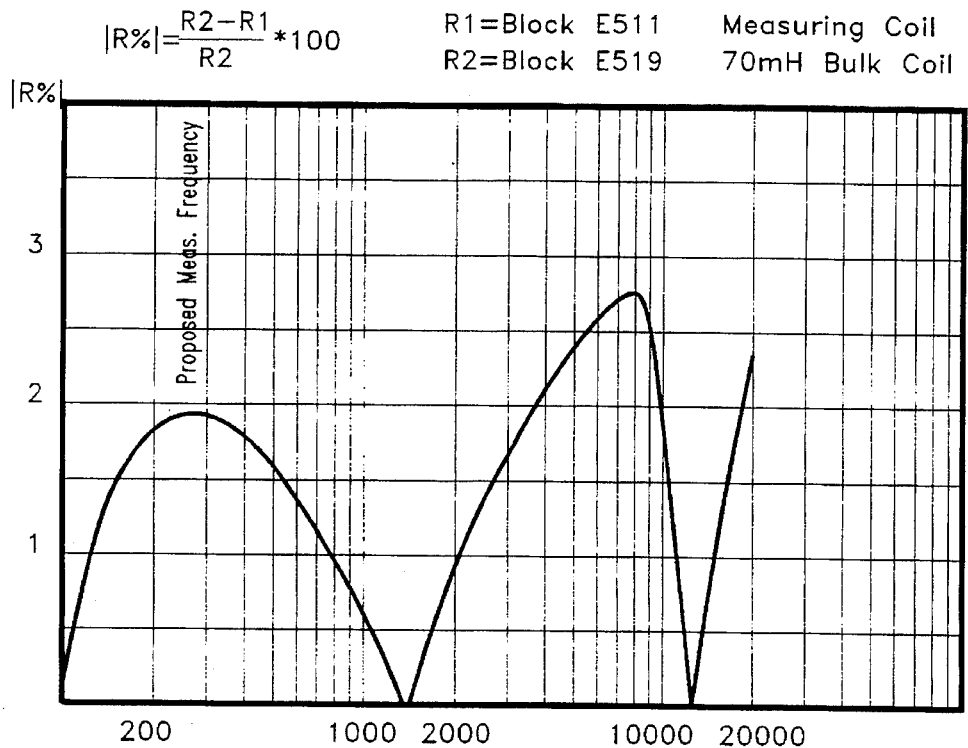
FIG. 9 is a graph of the sensitivity of the $R_S$ measurement to changes in resistance using the large block surrounding coil.
Figure 10:
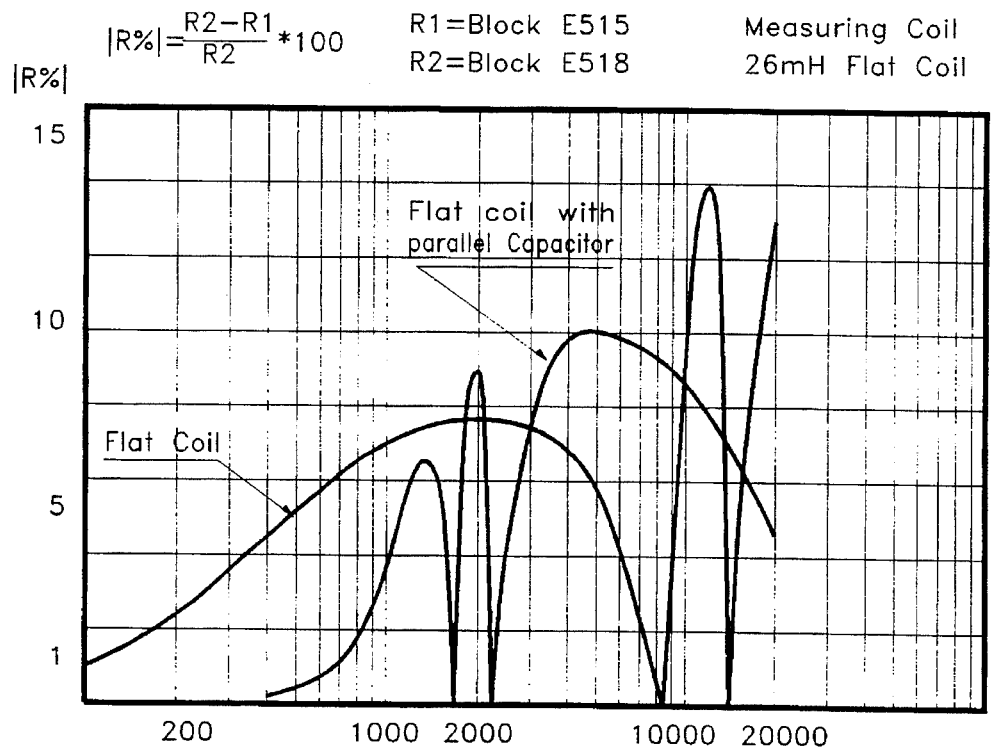
FIG. 10 is a graph of the sensitivity of the $R_S$ measurement to changes in resistance using the flat coil and flat coil with parallel capacitor.

In order to achieve maximum current penetration of the carbon block, a measurement frequency as low as possible should be chosen. However, as the frequency is lowered, the transformed carbon block resistance decreases to values comparable to the coil's DC copper resistance. At this point, variations of the copper resistance due to temperature changes adversely affect the accuracy of the measurements. Further, the upper frequency limit is determined by the skin depth and is about 2,000 Hz. The low frequency limit, given by value of the transformed cathode resistance is approximately 200 Hz. Depending on the coil and load combination, only specific frequency bands can be used to measure variations of bulk resistance. From two block measurements exhibiting large differences in R, the calculated magnitude of $\Delta R\%=R1-R2/R1\times100$ as a function of frequency. These calculations have been made for the large block surrounding coil, the flat coil, and the flat coil with parallel capacitor, and the results are illustrated in FIGS. 9 and 10. FIG. 10 illustrates that by adding a capacitor parallel to the coil, suitable frequency bands shift to lower frequencies. By adding an appropriate capacitor, the bands may be shifted to any frequency desired. In the preferred embodiments of the present application the suitable frequency bands are listed as follows:

Large Block Surrounding Coil 200 Hz±100 Hz

Flat Coil 2000 Hz±500 Hz

Flat Coil with Capacitor 1300 Hz±100 Hz or 2000 Hz±10 Hz.

Figure 11:
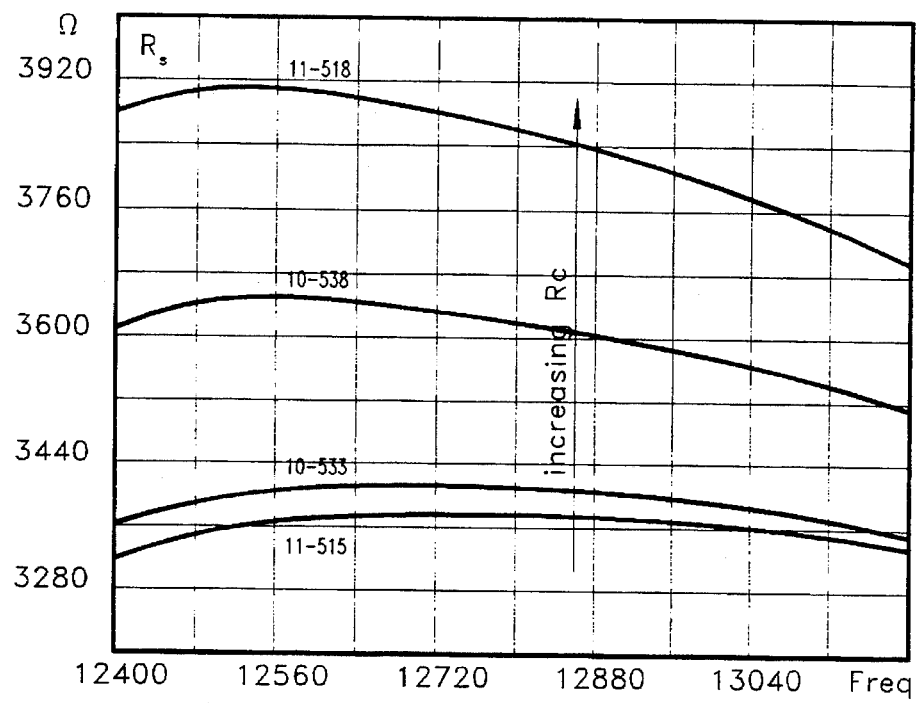
FIG. 11 is a graph of resistance measurements made with the flat coil at the resistance peak.
Figure 12:
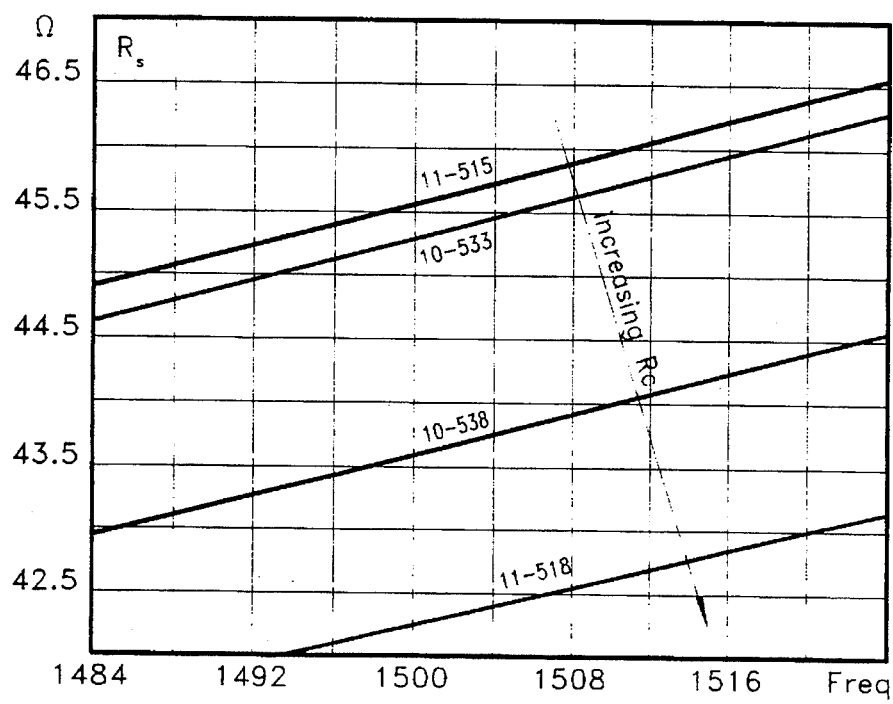
FIG. 12 is a graph of resistance measurements made with the flat coil at a suitable low frequency.
Figure 13:
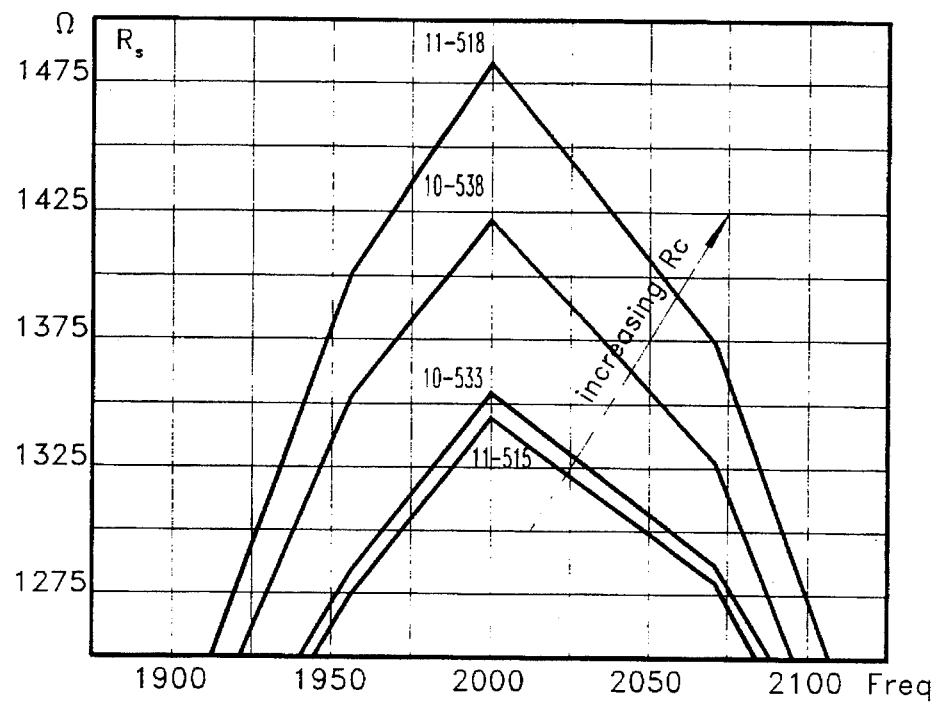
FIG. 13 is a graph of resistance vs. frequency for various samples at the resistance peak measured with the flat coil with parallel capacitor.
Figure 14:
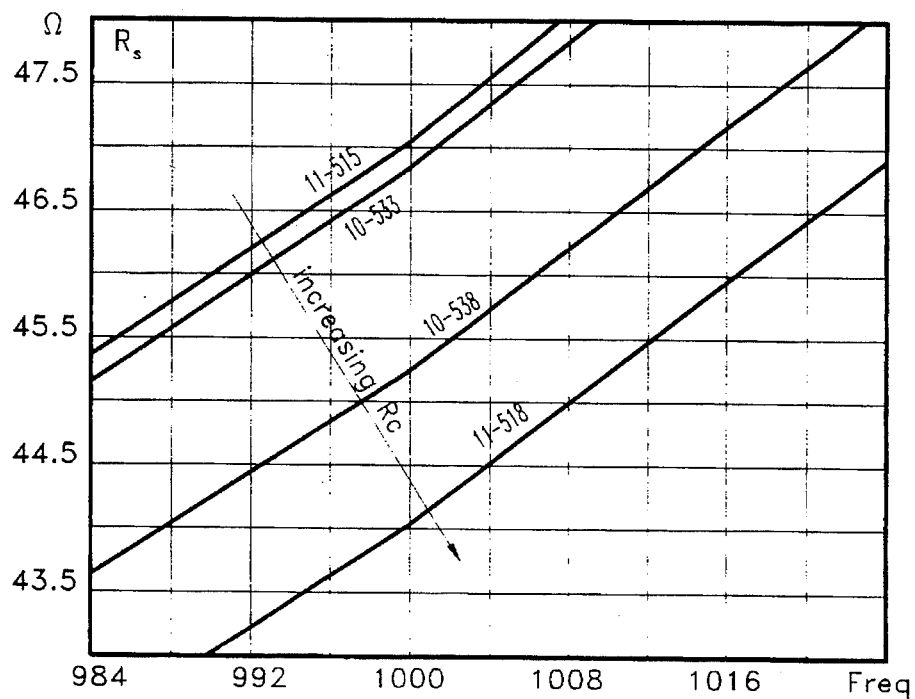
FIG. 14 is a graph of resistance vs. frequency for various samples at low frequency measured with the flat coil with parallel capacitor.

The resistance was measured for two groups of ten carbon blocks using the large block surrounding coil, the flat coil, and the flat coil with parallel capacitor. The two groups of carbon blocks were specially selected with regard to their position in a bake oven. The first group came from randomly selected sections 10-531 to 539 and the second group from randomly selected sections 11-510 to 519. In the baking oven, each position an anode might take in each slot in the oven, which is over 100 yards long, is given a specific designation such as the ones disclosed above. Since it is impossible to generate uniform heat over such a large area, the exact location of each block in the oven is recorded. The section 10 blocks were labeled with a "T" designation while the section 11 group has been given a "E" designation. Tests were performed at 200 frequency points from 20 Hz to 20,000 Hz. FIGS. 11–14 illustrate the resistance variation of two blocks for group 10 and two blocks of group 11. The blocks shown exhibit the largest variation in each group. FIGS. 11, 12 are measurements with the flat coil and FIGS. 13, 14 are measurements the flat coil with parallel capacitor. FIGS. 11 and 12 illustrate the peak resistance responses and FIGS. 12 and 14 illustrate the resistance response at a suitable frequency below the peak response. A reduction in bulk resistance is illustrated as a decrease in resistance in FIGS. 11 and 13 and an increase in FIGS. 12 and 14 (which agrees with the theoretical expectations discussed above).

In the range of interest, the accuracy of the measuring device is better than 0.05% of the measured value. This is less than 2 ohms in FIG. 11, less than 1 to 2 ohms in FIG. 13, and 0.025 ohms in FIGS. 12 and 14. Assuming, due to misplacement of the coils, and other factors on-site, that the instrument errors were multiplied by a safety factor of approximately 10, then the accuracy figures would be 20 ohms, 10 ohms, and 0.25 ohms, respectively. The differences in the curves shown for blocks 11-515 and 10-533 could, under these conditions be considered measuring errors. However, the difference between blocks 10-533 and 10-538 are so large compared with the worst case measurement error that they represent true differences in the bulk resistance of these blocks. A similarly large bulk resistance difference exists between blocks 10-538 and 11-518 (see FIGS. 11 and 13).

The difference in resistance between blocks 11-515 and 11-518 is approximately 10%. If it were possible to bring all the block resistance down to the value of block 11-515 or below, the reduction of nearly 10% would be feasible. Assuming all the resistance error is due to a change of resistivity, then the on-line system could detect a variation in resistivity of 30 µΩcm.

These results illustrate that the measuring method is sufficiently sensitive to measure changes of block resistance at selected frequencies to make these methods suitable for an on-line quality control method.

Next, the four-point resistivity measurement for measuring intrinsic resistivity of the carbon anode block will be discussed. As indicated above, two current carrying probes are placed on one surface of the rectangular block of conducting material and an electrical potential distribution is generated inside the conducting body and on its surface. For appropriately chosen contact locations, the potential difference between two points on the surface is primarily given by the resistivity of the conducting body. It is therefore, possible to calculate the resistivity from the potential difference measurement.

Figure 15:
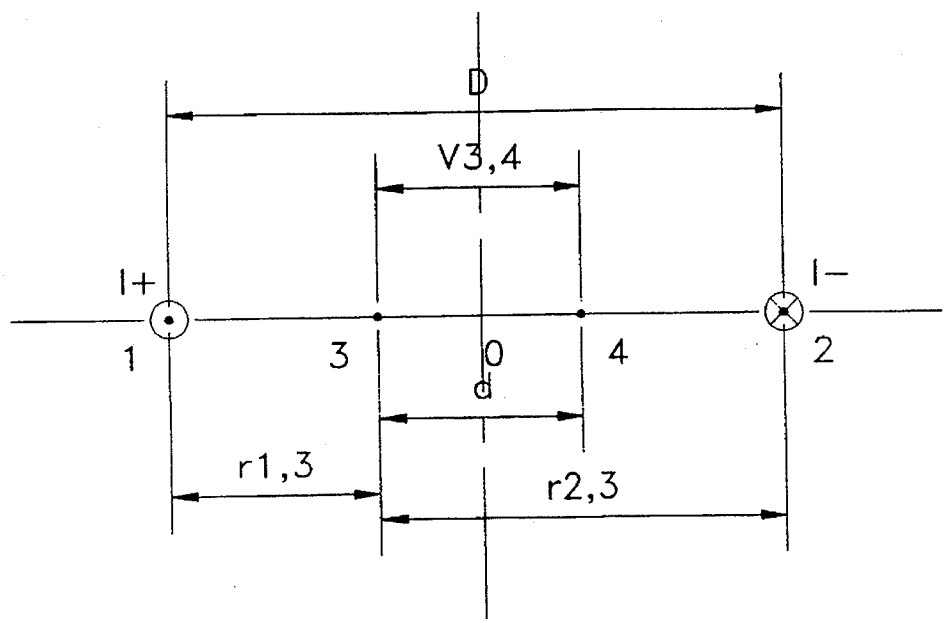
FIG. 15 is an illustration of a direct resistivity measurement.

Two current probes, separated by an appropriate distance from each other, are brought into contact with the carbon anode surface. A DC voltage is applied to the probe so that a current of 1 to 20 amps flows in the carbon anode. In a preferred embodiment, a current of 3 to 10 amps flows in the carbon anode. This current establishes an electric field on the carbon surface between the electrodes and beyond. The potential drop measured on the carbon surface is directly related to resistivity. Data taken utilizing this method yields resistivity measurements which are as good or better than the core samples discussed above with respect to conventional methods. The theory of the direct resistivity measurement is as follows. Two current carrying electrodes, illustrated in FIG. 15, separated by a distance D, which are in contact with a conducting infinite half-space, generate a potential distribution inside the conducting medium given by:

$$\phi(P) = \frac{I_p}{2\pi} \left( \frac{1}{r_{1p}} - \frac{1}{r_{2p}} \right)$$

Where:

$I_p$=the DC current and $r_{1p}$ and $r_{2p}$=radiant distances to point P.

Further, the potential difference between two symmetrically located points on a line connecting the two current probes is given by:

$$V_{3,4} = \frac{I_p}{\pi} \left( \frac{1}{r_{13}} - \frac{1}{r_{23}} \right)$$

Where:

$I_p$=the DC current and $r_{13}$ and $r_{23}$=radiant distances to point P.

Figure 16:
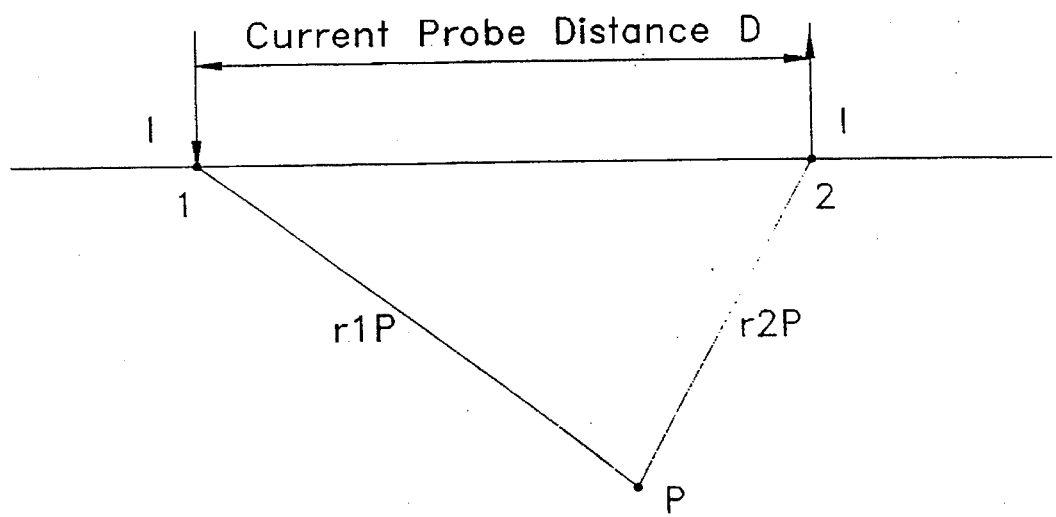
FIG. 16 is an illustration of an actual measuring setup for measuring direct resistivity.

FIG. 16 illustrates an actual measuring setup, where $r_{13}$ and $r_{23}$ are known constants. Further, I and $V_{3,4}$ are measured quantities from which the resistivity can be calculated by:

$$\rho = \frac{V_{3,4}}{I} \pi \frac{r_{13} r_{23}}{r_{13} - r_{23}} \; [\Omega m]$$

Where:

I=the DC current and $r_{13}$ and $r_{23}$=radiant distances to point P.

Figure 17:
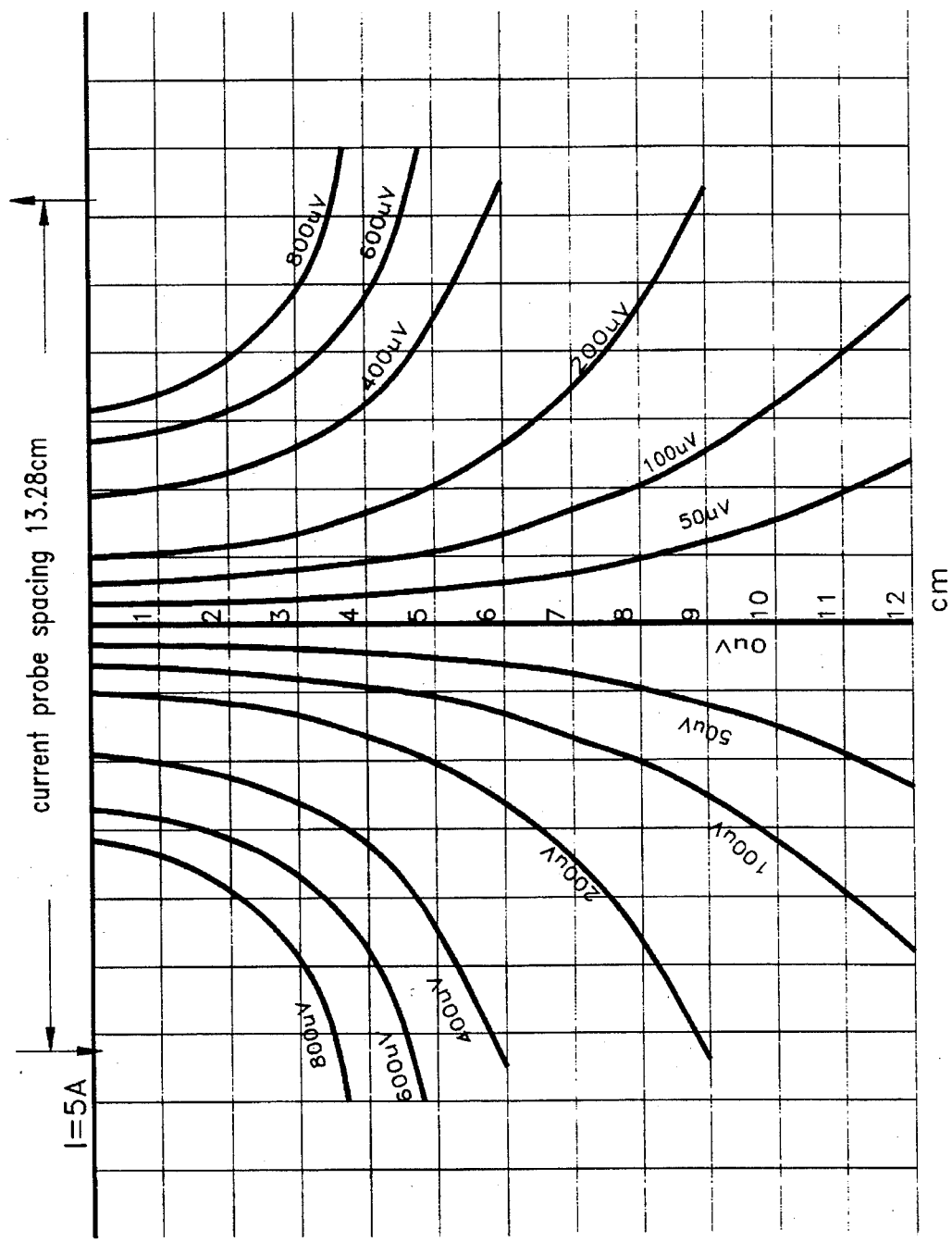
FIG. 17 is a graph of a calculated potential distribution for a resistivity of 5400 µΩcm and current probe spacing of 13.28 cm.

FIG. 17 illustrates the calculated equipotential lines for a resistivity of 5400 μΩcm. The reference potential (zero V) is the symmetry axis between the current probes.

Figure 18:
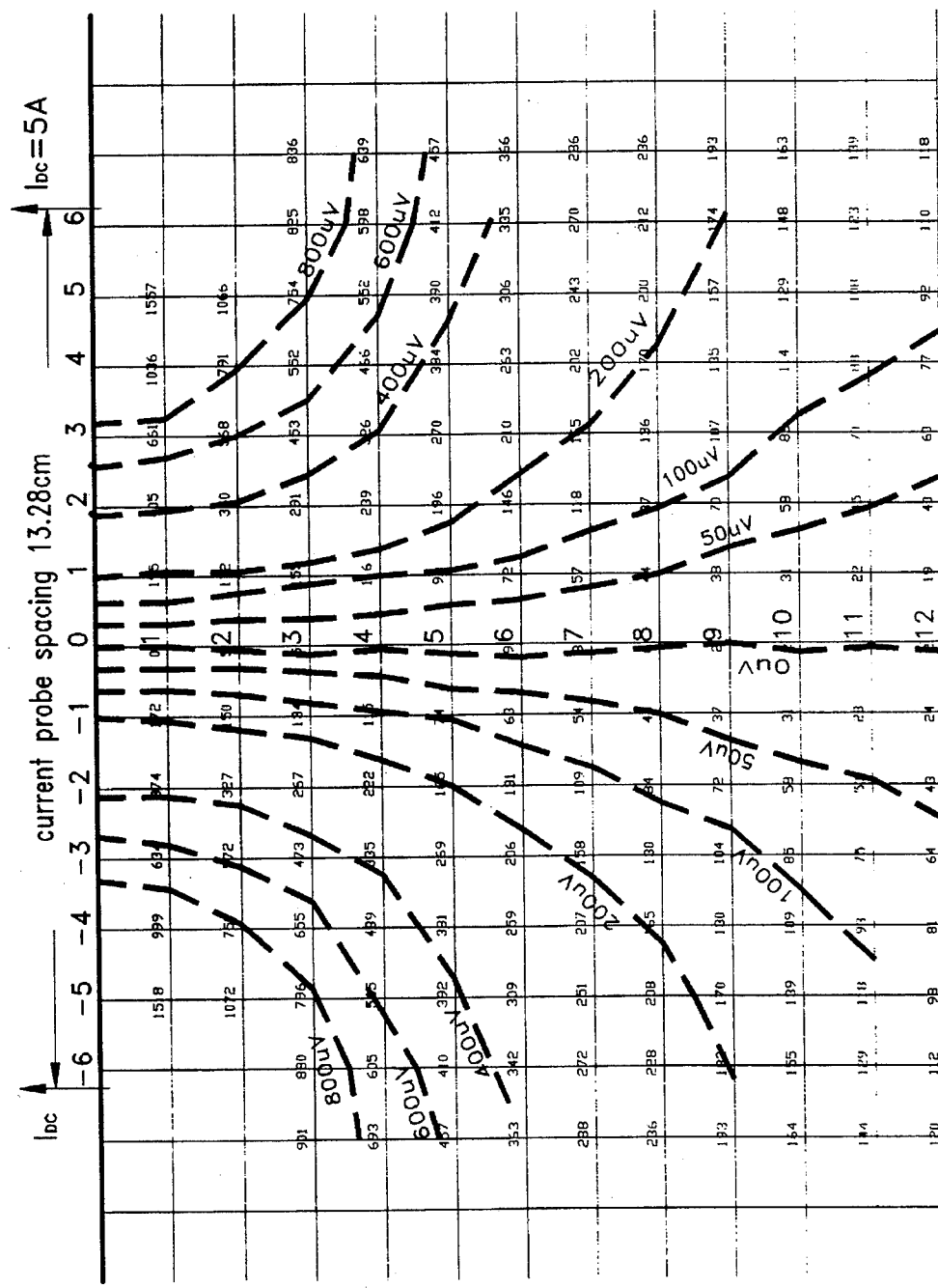
FIG. 18 is a graph of a measured potential distribution for a resistivity of 5400 µΩcm and current probe spacing of 13.28 cm.
Figure 19:
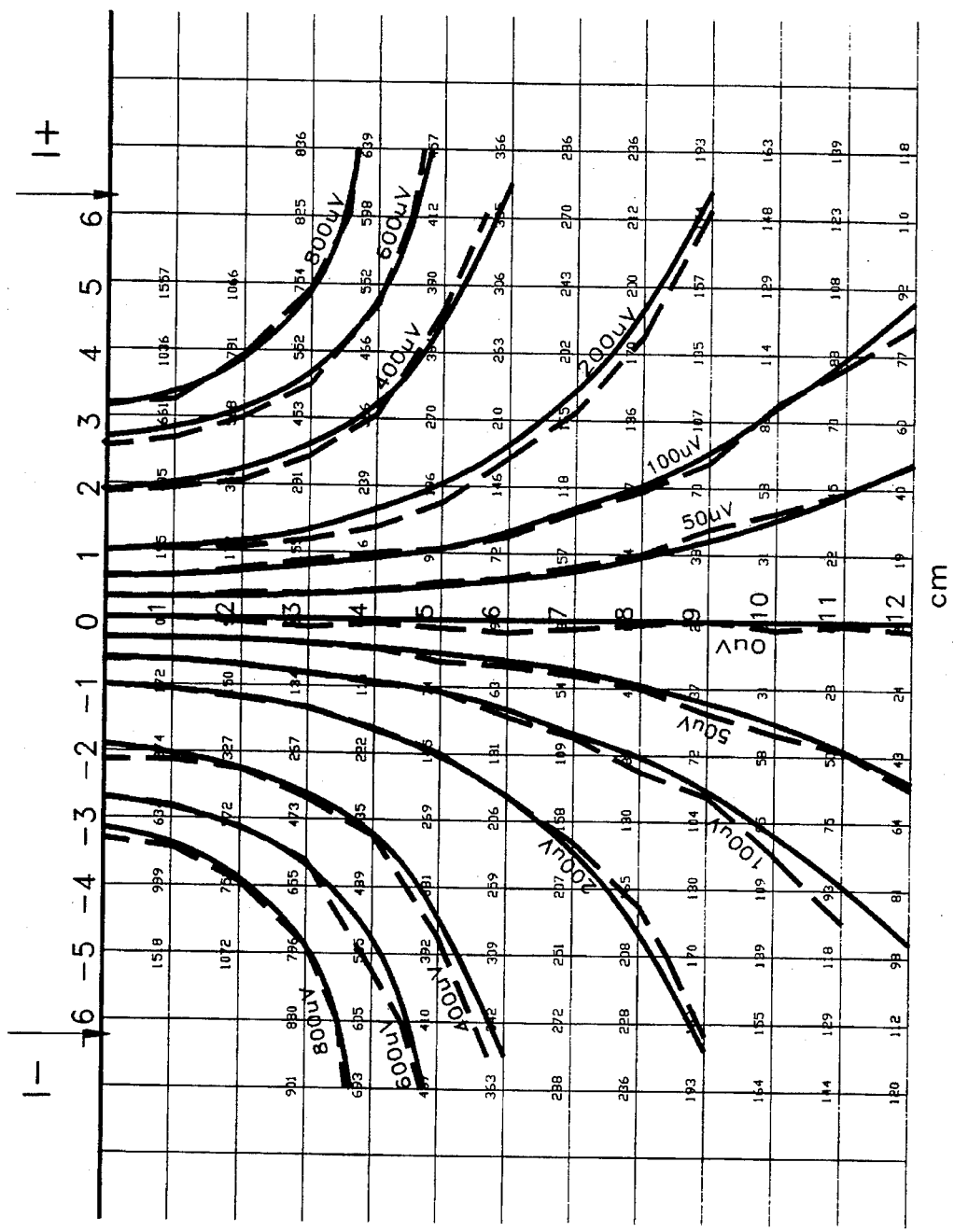
FIG. 19 is a graph of both the calculated and measured potential distributions of FIGS. 17 and 18.

FIG. 18 illustrates the results of actual measurements on a carbon anode. FIG. 19 is an overlay of a theoretical potential distribution illustrated in FIG. 17 and the measured potential distribution of FIG. 18.

Since carbon anode blocks are not infinite half spaces, it is necessary to experimentally establish the spacing of the potential and the current probe. A balance between the following contradictory requirements must be found. First, the current probe spacing should be small, compared to the size of the carbon block and the voltage probe spacing should be small compared with the current probe spacing. On the other hand, the spacing should be large so that the potential difference measured is large compared to the contact potential, therefore, the current should be high in order to produce a large potential difference. However, too high a current will raise the temperature of the carbon block which in turn will change the resistivity near the contact.

Figure 20:
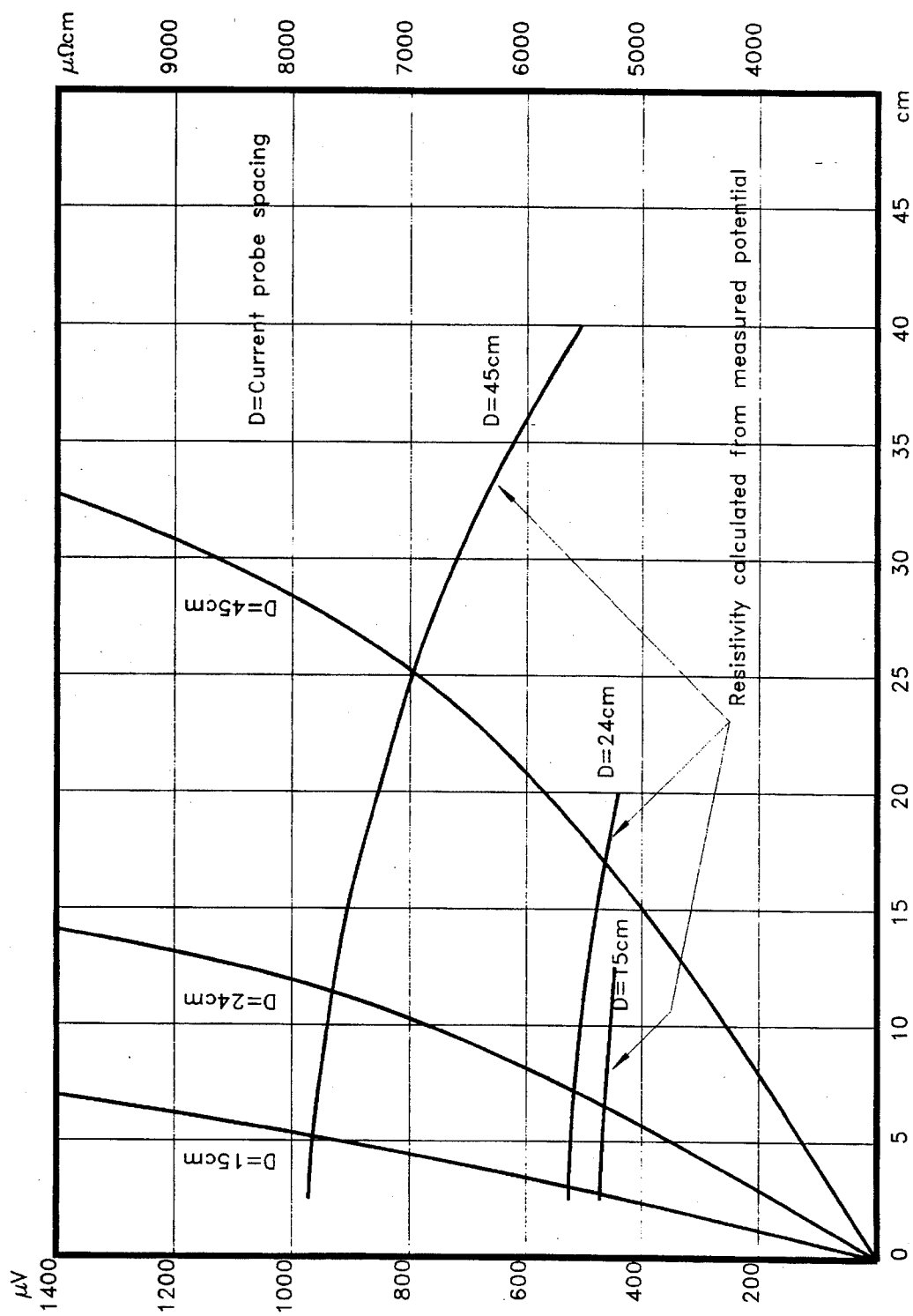
FIG. 20 illustrates the influence of the potential probe spacing on the voltage drop and resistivity for three current probe spacings.

Experimental tests illustrate that at least a current of 1 amp is necessary to produce a sufficiently large voltage drop to be reliably measured. Further, up to 20 amps may be acceptable depending on how long it takes to make the measurement before the temperature rise becomes too large. FIG. 20 illustrates the influence of the potential probe spacing on the voltage drop and resistivity for three current probe spacings. When the current probe spacing is large compared to the block size, the measured resistivity is too high and strongly dependent upon the voltage probe spacing. As the current probe spacing decreases, the measured resistivity approaches the actual resistivity of the block and becomes essentially independent of the voltage probe spacing. The fact that the resistivity becomes independent of the voltage probe spacing for small current probe spacings indicates that the measuring parameters approach the theoretical model.

Figure 21:
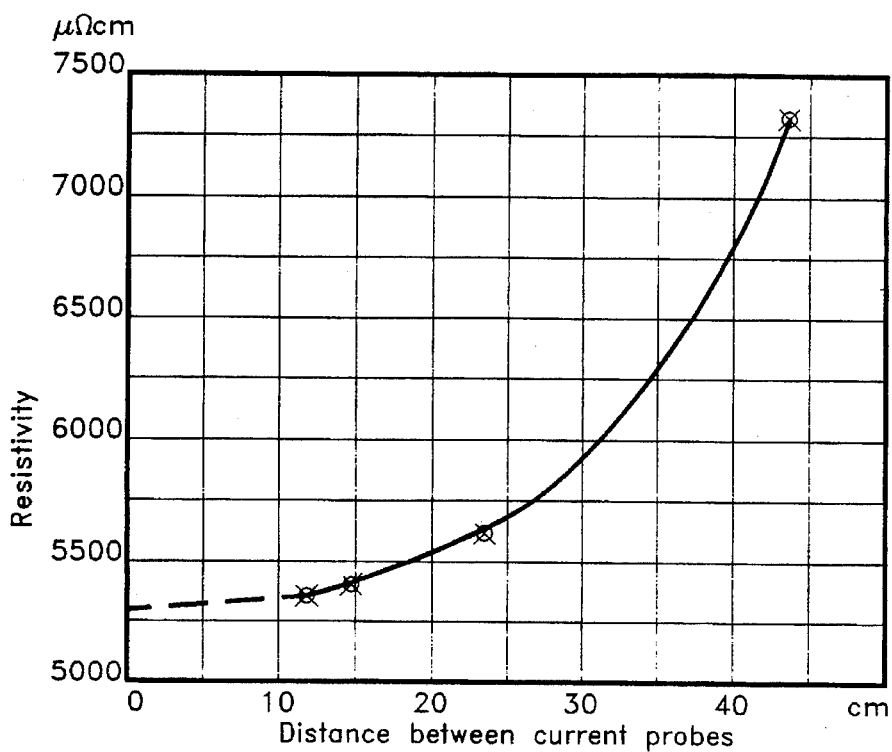
FIG. 21 illustrates the resistivity as a function of current probe spacing for a voltage probe spacing of ⅓ the current probe spacing.

In the preferred embodiment of the present invention, the current probe spacing is 10 to 16 cm, while the voltage probe spacing is ⅓ to ½ of the current probe spacing. FIG. 21 illustrates the resistivity as a function of current probe spacing for a voltage probe spacing of ⅓ of the current probe spacing. The extrapolation of this curve to a current probe spacing of 0 cm gives the intrinsic resistivity of the carbon material.

Figure 22:
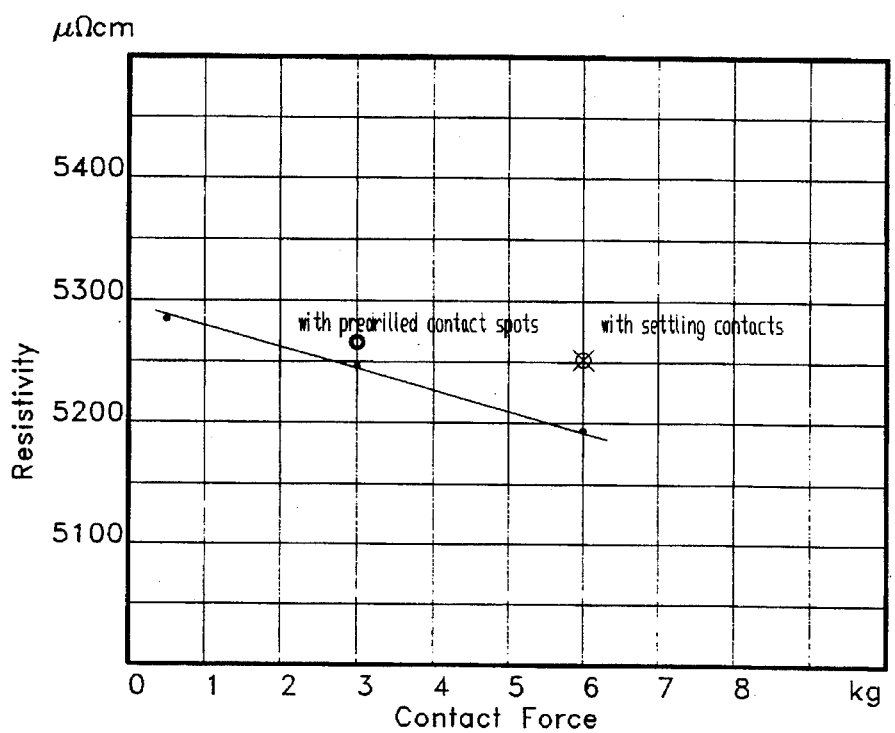
FIG. 22 is a graph of resistivity vs. contact force.

As a result, it is possible to measure resistivity without utilizing core samples. FIG. 22 illustrates that the quality of the current contacts does not significantly influence the accuracy of the measurement. In reality, contact resistance is no influence whatsoever, in contrast, the current probe's surface area form, in contact with the carbon block, influences the potential distribution. The accuracy of the measurement is therefore mainly influenced by the roughness of the carbon surface, and the wear and tear of the current probes. As a result, the current probe tips should be made of silicon carbide or other similar material in order to ensure the current probe tips last as long as possible. Once the four point resistivity and eddy loss measurements have been obtained, as described above, it is possible to establish a measure of anode quality. It is possible to distinguish the following four broad anode quality regions, illustrated in Table 1.

| 4 Point Resistivity | Eddy Losses | Anode Quality |
| --- | --- | --- |
| Low | Low | Medium |
| Low | High | Excellent |
| High | Low | Low |

| 4 Point Resistivity | Eddy Losses | Anode Quality |
|---|---|---|
| High | High | Medium |

The values for eddy losses and anode quality will vary according to differences between raw material suppliers, variances within the raw material from a single supplier and changes to the production processes for block forming and baking.

Using the measurements disclosed herein and the Table above, the primary aluminum producer is able to automatically test anodes nondestructively in an in-line test setup for internal flaws and low resistivity. As a result, low quality anodes may be discarded early in production. Further, the system and method disclosed herein may be implemented on a computer with software generated based on this disclosure to automatically analyze the carbon anodes.

With the invention being thus described, it will be obvious that the same may be varied in many ways. Such variations are not to be regarded as a departure from the spirit and scope of the invention and all such modifications as would be obvious to one skilled in the art or intended to be included within the scope of the following claims.

What is claimed:

1. A system of automatic in-line electrical quality control of a carbon anode for use in producing primary aluminum, comprising:
   eddy current loss measuring means for measuring an eddy-current loss of the carbon anode;
   bulk resistivity determining means for measuring a bulk resistivity of the carbon anode; and
   electrical quality determining means for determining the electrical quality of the carbon anode for use in producing the primary aluminum according to the measured eddy-current loss and the measured bulk resistivity of the carbon anode.

2. The system of claim 1, said eddy current loss measuring means including,
   coil means, excited by an alternating current, for inducing a current in the carbon anode, and
   measuring means for measuring a reflected impedance of said coil means, representative of the eddy current loss of the carbon anode.

3. The system of claim 2, wherein a measurement frequency band of the induced current is 2000 Hz±200 Hz.

4. The system of claim 1, wherein said electrical quality determining means is a computer.

5. The system of claim 2, wherein a low reflected impedance indicates the presence of flaws in the carbon anode.

6. The system of claim 2, wherein said coil means is a large block surrounding coil.

7. The system of the claim 2, wherein said coil means is a flat coil.

8. The system of claim 2, wherein said coil means includes a flat coil and a capacitor.

9. The system of claim 2, wherein said measuring means is a computer addressable impedance measuring bridge.

10. The system of claim 2, wherein the induced current in the current anode flows in a same direction as a DC operating current flow when the carbon anode is used in producing the primary aluminum.

11. The system of claim 6, further comprising wood or plastic rollers for moving the carbon anode into the large block surrounding coil.

12. The system of claim 8, wherein changing a value of said capacitor shifts the measurement frequency band.

13. The system of claim 1, said bulk resistivity determining means including,
   two current carrying probes for applying a current to a surface of the carbon anode, and
   two potential probes for measuring a potential difference at the surface of the carbon anode.

14. The system of claim 13, wherein said two current carrying probes and said two potential probes are linearly arranged with said two current carrying probes located at each end of the linear arrangement.

15. The system of claim 14, wherein spacing between said two potential probes is ⅓ to ½ a spacing of said two current carrying probes.

16. The system of claim 15, wherein the spacing of said two current carrying probes is 10 to 16 cm.

17. The system of claim 13, wherein said two current carrying probes and said two potential probes are spring loaded and include stops to ensure a contact force between each of the probes and the surface of the carbon anode is within a certain range.

18. The system of claim 13, wherein the current supplied to the surface of the carbon anode is 5 to 10 amps.

19. The system of claim 18, wherein a potential distribution generated in the carbon anode equals:

$$\phi(P) = \frac{I_p}{2\pi} \left( \frac{1}{r_{1p}} - \frac{1}{r_{2p}} \right)$$

Where:
   $\phi(P)$=the potential distribution at point P;
   $I_p$=a DC current; and
   $r_{1p}$ and $r_{2p}$=radiant distances to point P.

20. The system of claim 19, wherein the potential difference equals:

$$V_{3,4} = \frac{I_p}{\pi} \left( \frac{1}{r_{13}} - \frac{1}{r_{23}} \right)$$

Where:
   $V_{3,4}$=the potential difference;
   $I_p$=the DC current, and
   $r_{13}$ and $r_{23}$=radiant distances to point P.

21. A method of automatic in-line electrical quality control of a carbon anode for use in producing primary aluminum, comprising the steps of:
   (a) measuring an eddy-current loss of the carbon anode;
   (b) measuring bulk resistivity of the carbon anode; and
   (c) determining the electrical quality of the carbon anode for use in producing the primary aluminum according to the measured eddy-current loss of said step (a) and the measured bulk resistivity of said step (b).

22. The method of claim 21, said step (a) including the sub-steps of:
   (a)(1) inducing a current in the carbon anode, and
   (a)(2) measuring a reflected impedance representative of the eddy current loss of the carbon anode.

23. The method of claim 22, wherein a measurement frequency band of the induced current is 2000 Hz±200 Hz.

24. The method of claim 21, wherein said step (c) is performed by a computer.

25. The method of claim 22, wherein a low reflected impedance indicates the presence of flaws in the carbon anode.

26. The method of claim 22, wherein the current is induced using a large block surrounding coil.

27. The method of the claim 22, wherein the current is induced using a flat coil.

28. The method of claim 22, wherein the current is induced using a flat coil and a capacitor.

29. The method of claim 22, wherein the reflected impedance is measured with computer addressable impedance measuring bridge.

30. The method of claim 22, wherein the induced current in the current anode flows in a same direction as a DC operating current flow when the carbon anode is used in producing the primary aluminum.

31. The method of claim 26, wherein wood or plastic rollers move the carbon anode into the large block surrounding coil.

32. The method of claim 28, wherein changing a value of the capacitor shifts the measurement frequency band.

33. The method of claim 21, said step (b) including the sub-steps of, (b) (1) applying a current to a surface of the carbon anode, and (b) (2) measuring a potential difference at the surface of the carbon anode.

34. The method of claim 33, wherein the current is applied by two current carrying probes and the potential difference is measured with two potential probes and the four probes are linearly arranged with the two current carrying probes located at each end of the linear arrangement.

35. The method of claim 34, wherein spacing between the two potential probes is ⅓ to ½ a spacing of the two current carrying probes.

36. The method of claim 35, wherein the spacing of the two current carrying probes is 10 to 16 cm.

37. The method of claim 33, wherein the two current carrying probes and the two potential probes are spring loaded and include stops to ensure a contact force between each of the probes and the surface of the carbon anode is within a certain range.

38. The method of claim 33, wherein the current supplied to the surface of the carbon anode is 5 to 10 amps.

39. The method of claim 38, wherein a potential distribution generated in the carbon anode equals:

$$\phi(P) = \frac{I_p}{2\pi} \left( \frac{1}{r_{1p}} - \frac{1}{r_{2p}} \right)$$

Where:

$\phi(P)$=the potential distribution at point P;

$I_p$=a DC current; and $r_{1p}$ and $r_{2p}$=radiant distances to point P.

40. The method of claim 39, wherein the potential difference equals:

$$V_{3,4} = \frac{I_p}{\pi} \left( \frac{1}{r_{13}} - \frac{1}{r_{23}} \right)$$

Where:

$V_{3,4}$=the potential difference;

$I_p$=the DC current, and $r_{13}$ and $r_{23}$=radiant distances to point P.

* * * * *

UNITED STATES PATENT AND TRADEMARK OFFICE
CERTIFICATE OF CORRECTION

PATENT NO. : 5,473,248
DATED : December 5, 1995
INVENTOR(S) : Paul R. Haldemann, Fawzi P. Emad It is certified that error appears in the above-indentified patent and that said Letters Patent is hereby corrected as shown below:

On title page, at (54) change "METHOD AND APPARATUS FOR NON-DESTRUCTIVELY DETECTING FLAWS IN A CARBON ANDODE"

to "METHOD AND APPARATUS FOR NON-DESTRUCTIVELY DETECTING FLAWS IN A CARBON ANODE"

also, at (75) Inventors, change incorrect spelling of second inventor, "EMAN P. FAWZI" to "FAWZI P. EMAD".

Signed and Sealed this

Twenty-third Day of April, 1996

Attest:

BRUCE LEHMAN

*Attesting Officer*    *Commissioner of Patents and Trademarks*